United States Patent
Korenman et al.

[19]

[11] Patent Number: 6,067,468
[45] Date of Patent: *May 23, 2000

[54] APPARATUS FOR MONITORING A PERSON'S PSYCHO-PHYSIOLOGICAL CONDITION

[75] Inventors: Ernesto Marcelo Dario Korenman, Wembley; Tuvi Orbach, London; Bernard William Watson, Harpenden, all of United Kingdom

[73] Assignee: Ultramind International Limited, Tel Hashomer, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 08/754,102

[22] Filed: Nov. 20, 1996

Related U.S. Application Data

[63] Continuation of application No. 08/190,163, filed as application No. PCT/GB92/01477, Aug. 7, 1992, abandoned.

[30] Foreign Application Priority Data

Aug. 7, 1991 [GB] United Kingdom .................... 9117015

[51] Int. Cl.[7] ........................................ G06F 1/00
[52] U.S. Cl. ............................................... 600/547
[58] Field of Search .................. 600/21, 26, 27, 600/28, 300, 481, 482, 483, 484, 485, 500, 527, 528, 533, 547

[56] References Cited

U.S. PATENT DOCUMENTS

| | | | |
|---|---|---|---|
| 3,590,497 | 7/1971 | Darby . | |
| 3,870,034 | 3/1975 | James . | |
| 4,006,539 | 2/1977 | Slomski . | |
| 4,009,708 | 3/1977 | Fay, Jr. ................................. | 128/2.05 |
| 4,030,483 | 6/1977 | Stevens ................................ | 128/2.05 |
| 4,037,332 | 7/1977 | Petrusinsky . | |
| 4,063,410 | 12/1977 | Welling ................................. | 58/38 R |
| 4,150,284 | 4/1979 | Trenkler et al. . | |
| 4,184,485 | 1/1980 | Agoston ................................ | 128/670 |
| 4,354,505 | 10/1982 | Shiga ................................... | 128/732 |
| 4,444,199 | 4/1984 | Shafer .................................. | 128/691 |
| 4,464,121 | 8/1984 | Perelli .................................. | 434/236 |
| 4,683,891 | 8/1987 | Cornellier et al. .................... | 128/630 |
| 4,730,253 | 3/1988 | Gordon . | |
| 4,751,642 | 6/1988 | Silva et al. . | |
| 4,800,893 | 1/1989 | Ross et al. . | |
| 4,812,126 | 3/1989 | Gilliksen ............................... | 434/238 |
| 4,894,777 | 1/1990 | Negishi et al. . | |

(List continued on next page.)

OTHER PUBLICATIONS

"TRS–80 Strings; Biofeedback and color Photos" Gray, Stephen; Creative Computing Oct. 1984.

"Computer System Response Time & Psychophysiological. etc" Boggs et al.; IEEE; 1982.

"Biofeedback Replaces Keyboard, Joysticks" Chin ; 1984 ; Computers in Psychiatry/Psychology.

IPAT Catalog of Psychological Assessment Instruments, Computer Interpretive Services, and Books, 1990–91, pp. 1–38.

Dialog Record—Furnham et al., "Measuring locus of control . . . ," *British Journal of Psychology,* v84, n4, Nov. 1993, p. 443 (37).

Dialog Record—Valla et al., "A structured pictorial questionnaire to assess DSM–III–R–based diagnoses in children," *Journal of Abnormal Child Psychology,* v22, n4, Aug. 1994, p. 403(21).

*Primary Examiner*—Robert L. Nasser
*Attorney, Agent, or Firm*—Breiner & Breiner

[57] ABSTRACT

The running of a program, designed to train the user to control one or more aspects of his or her psycho-physiological state, is controlled by signals representative of a psycho-physiological parameter of the user, e.g., galvanic skin resistance. This may be detected by a sensor unit with two contacts on adjacent fingers of a user. The sensor unit is separate from a receiver unit which is connected to a computer running the program.

7 Claims, 5 Drawing Sheets

U.S. PATENT DOCUMENTS

| | | | |
|---|---|---|---|
| 4,931,934 | 6/1990 | Snyder . | |
| 4,949,726 | 8/1990 | Hartzell et al. . | |
| 5,016,213 | 5/1991 | Dilts et al. | 600/547 |
| 5,219,322 | 6/1993 | Weathers . | |
| 5,228,449 | 7/1993 | Christ et al. | 128/691 |
| 5,235,363 | 8/1993 | Vogeley et al. . | |
| 5,253,168 | 10/1993 | Berg | 364/413.01 |
| 5,344,324 | 9/1994 | O'Donnell et al. . | |
| 5,564,433 | 10/1996 | Thorton | 600/27 |
| 5,681,259 | 10/1997 | August | 600/27 |

APPARATUS FOR MONITORING A PERSON'S PSYCHO-PHYSIOLOGICAL CONDITION

This is a continuation of application Ser. No. 08/190,163 filed on Feb. 7, 1994, now abandoned, which was filed as PCT/GB92/01477 on Aug. 7, 1992.

FIELD OF INVENTION

This invention relates to the operation of computer systems, particularly, though not exclusively, to computer-assisted learning.

BACKGROUND OF INVENTION

In recent years, the development of so-called "personal computers", or PCs for short, has enabled computing power to be made available to millions of people. In parallel with the development of the hardware, there has been major growth in the amount of software being written. In a PC system, the user operates the PC by first controlling it with the aid of software to be ready to operate in accordance with a desired programme, and then inputting data and producing output data from the PC.

In order to input data, a variety of devices may be used, the most common of which is a keyboard. The most common output device is a visual display unit (VDU) or screen on which the results of operations within the computer may be displayed to be read (if expressed in words) and/or viewed by the user.

Other input may be fed into the computer in known fashion. For example, most PCs have one or more communications ports which can send or receive data in the form of digital signals. The data can be received, e.g. from sensor units via appropriate interface circuits, or from other PCs. It is known that a very wide variety of sensors may be used, including sensors which sense human physiological parameters, for example blood pressure or electrical currents in the body (in computer-controlled electrocardiogram or electroencephalogram systems). However, up till now, such uses have been mainly confined to those where the computer user has not been the same person as the person under test.

An example where such use is not confined to those where the computer user has not been the same person is shown in published International Application WO 86/01317 which discloses using galvanic skin resistance to input data into a computer, and deals specifically with the electronics necessary to overcome the problem of the very wide range of galvanic skin resistances that may be sensed over a period of time and from one user to another.

Published International Application WO89/02247 discloses a system whereby a PC owner may monitor his or her heart activity using a simple probe which connects to the input of the computer. A suitable programme must be loaded into the computer in order to enable display or printout representative of the user's cardiac function to be effected. Published European Patent Application 0176220 also discloses using a computer to monitor a user's heart.

Published International Application WO 91/01699 discloses use of a computer and suitable sensor means to offer limited mobility and limb movement patients are means of operating a computer. United States Patent Specification 4894777 uses sensor means to detect when a computer user ceases to concentrate on the subject they should be concentrating on, and published UK Patent Specification 2079992A discloses using a sensor means and microcomputer to predict the fertility period in a woman's menstrual cycle.

GENERAL DESCRIPTION OF THE INVENTION

In accordance with the present invention, there is provided apparatus for testing an aspect of one or more users psycho-physiological condition which provides an information display which may be viewed by the user and which at least provides information about, or indication of, the user's substantially current psycho-physiological condition reflected by that aspect being tested, and which may provide one or more stimuli to the user, the apparatus comprising a computer system, an input device, and software capable of interpreting data input from the input device and displaying the required information, wherein the input device comprises a sensor unit and a receiver unit;

the sensor unit is adapted to be attached to one or more users and periodically to sense at least one psycho-physiological condition and to transmit data corresponding to the user's psycho-physiological condition to the receiver unit;

the receiver unit being adapted to input the data concerning the user's condition into the computer system;

the sensor unit and the receiver unit being separate from each other.

Such apparatus, providing the programme or software is appropriate, may also be used to enable control of a computer game by way of the user's control of one or more of his or her psycho-physiological parameters. Thus, the precise running of programme may depend on both conscious input from the user and on one or more psycho-physiological parameters of the user.

In using the apparatus, the user interacts with the programmed computer via two channels, the conscious voluntary channel, e.g. mediated via a standard keyboard or via keys on a keypad forming part of the sensor unit and an unconscious involuntary channel, e.g. mediated via a galvanic skin resistance (GSR) sensor and appropriate circuitry to feed a signal representative of GSR to the receiver and thence the computer system. It is known that GSR correlates with arousal/relaxation. Thus, the operation of an interactive learning programme or of a games programme may be mediated not merely by the user's keyboard input but by his or her state of arousal. For example, the speed at which a game is to be played may vary depending on GSR, giving relaxed players an advantage over tense ones. The 'game' may be of a type designed to teach definite behavioural skills. As in other computer games, performance during the game is monitored and quantified, and the dexterity shown in the different tasks is measured, for example, the game may test for and train fast recovery after psychomotor challenge. The user may be made to perform a pre-defined psychomotor, such as time response or co-ordination tasks and should then return immediately to the same state of arousal prior to the challenge. Whether he or she returns to an increased or decreased level of arousal may be reflected by animation refinements, e.g. the shape and configuration of a display icon. Alternatively, such a programme may teach the user to reach a predetermined level of arousal and remain within a range around that level for a certain period of time, and to detach himself or herself from external stimuli such as computer sound, mind information, etc., remaining at a certain level of arousal.

In order to put the invention into effect, it is necessary to have computer apparatus arranged to provide a visual output under control of a programme, the output being dependent on input via the keyboard and input via a psycho-physiological parameter sensor located to monitor such a parameter of the user. In a preferred form, the sensor unit communicates with the receiver unit connected to the computer input via a non-physical connection, such as an electromagnetic cordless link, thus enabling the user to 'forget' that he or she is interacting with the computer. An infrared transmitter-receiver system is the preferred non-physical connection. Such systems are inexpensive and reliable, and, on account of their use in remote controllers for electrical or electronic apparatus (garage doors, video recorders, CD players), are widely available.

The range of application of the present invention is very wide. One particular valuable field is in computer-assisted learning, where the 'teaching' computer may be able to modify its part in an interactive programme in accordance with the condition of the user. Thus, like a human teacher, the computer may go slower if it senses that its pupil is tired, or showing signs of stress related to incomprehension, or may even judge the user's state as non-receptive and refuse to teach him or her further until the appropriate input is received, showing that the user is receptive to teaching again.

The programme may be arranged to display to the user an indication of the psycho-physiological parameter measured, thus enabling the user who so wishes to try and consciously moderate or modify their response in a fashion analogous to 'biofeedback' techniques. For example, a teaching programme could be arranged to display as a variable height bar or variable colour spot the arousal state of the user, determined from GSR and/or other measurements.

In principle, the display viewed by the user may vary very widely and consist of graphics, animation, wording or combinations of these. The timing of image display will be controlled by the programme. The programme may be one which displays subliminal stimuli via the screen as well as consciously perceptible images.

The conscious interaction between computer system and user may also be mediated via one or more standard usually manually controlled devices, e.g. keyboard, mouse, joystick. The unconscious interaction via sensor and receiver may rely on one or more parameters, for example GSR, brain or cardiac electrical signals (as in EEG and ECG monitoring), heart or pulse rate, skin temperature, or others. In all such cases, it is highly desirable that the parameter is sensed and data fed to the computer as a result in an unnoticeable way, so leaving the unconscious input to the computer easily forgotten about so that it does not distract the user from concentrating on interacting with the computer consciously.

BRIEF DESCRIPTION OF DRAWINGS

Embodiment of apparatus in accordance with the invention will now be described, by way of example, with reference to the accompanying drawings, in which.

DESCRIPTION OF PRESENTLY PREFERRED EMBODIMENTS

Figure 1:
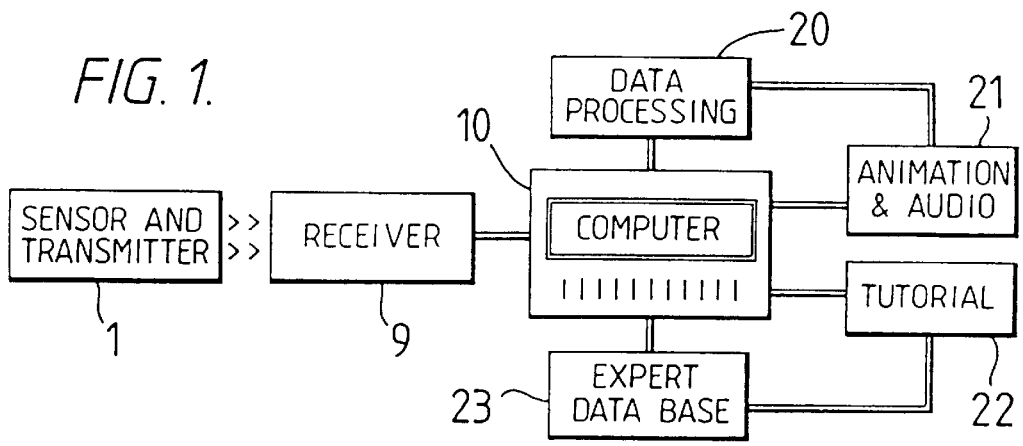
FIG. 1 is a block diagram of apparatus for use in interactive training mediated by psycho-physiological performance.
Figure 2A:
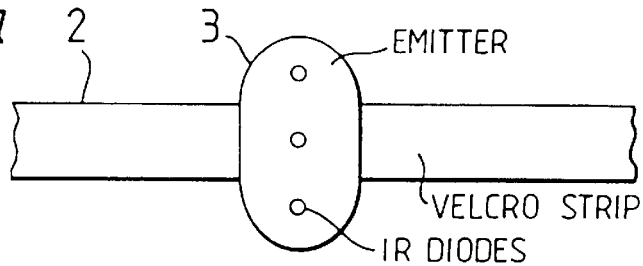
FIGS. 2a and 2b show front and back views of a sensor for attachment to a person's wrist.
Figure 2B:
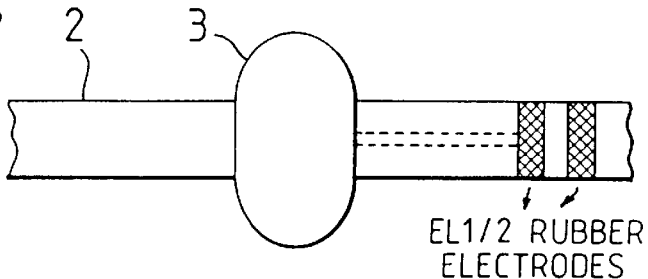
Figure 2C:
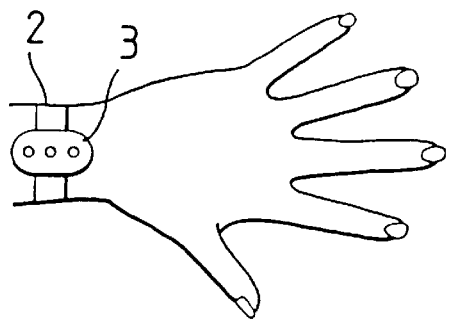
FIGS. 2c and 2d show front and back views of a hand and wrist with the sensor of FIGS. 2a and 2b attached.
Figure 2D:
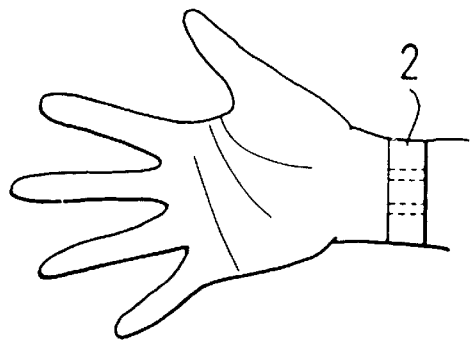

In the apparatus of FIG. 1, signals representative of a parameter being sensed by a sensor are sent via an infrared link from a sensor and transmitter 1 to a receiver 9.

Figure 3:
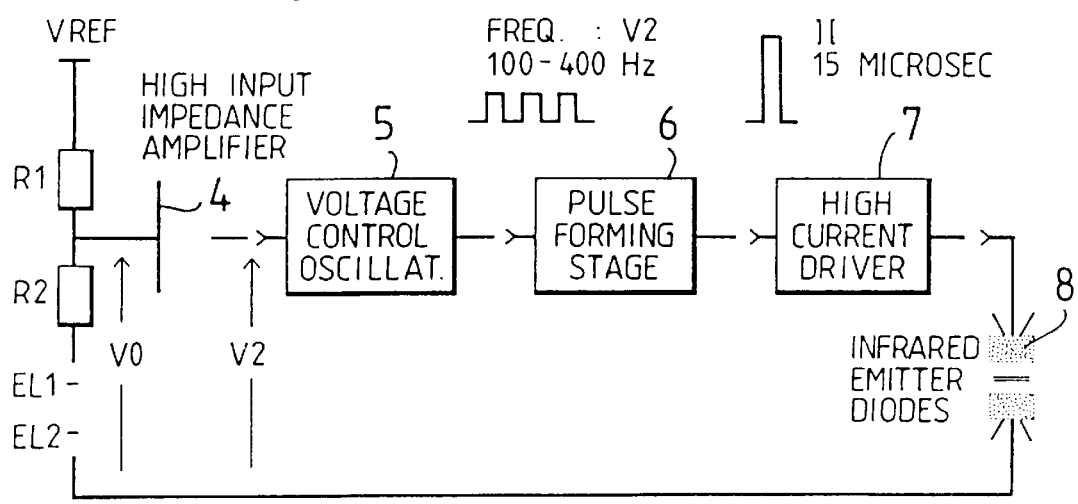
FIG. 3 is a block diagram of an infrared biotelemetry transmitter.

The sensor comprises an attachable wrist-belt 2 (FIGS. 2a to 2d) carrying two pads which abut the skin and a microelectronic device to detect the galvanic skin resistance (GSR) of the wearer. The device is mounted in a watch-like case 3 and connected electrically to two rubber skin electrodes EL1 and EL2. A stabilised voltage Vref (FIG. 3) is applied in series with resistors R1 and R2 and the two electrodes EL1 and EL2. When the wearer's skin resistance increases, the voltage between the electrodes and the output voltage V0 which feeds the input to a high impedance buffer amplifier 4, both rise. A corresponding signal is emitted by infrared emitter diodes to be received by a receiver 9.

Galvanic skin resistance levels can vary over a range of over 100 to 1. The simple input arrangement illustrated in detail in FIG. 3 offers two special benefits for GSR measurement. First, the output voltage never saturates, even though its response may be low at extreme resistance values; and second, over a useful resistance range of about 30 to 1, the output voltage responds approximately linearly to the logarithm of skin resistance. These features provide an orderly and stable compression of the large input parameter range, allowing satisfactory transmission within the rather restricted, typically 4 to 1, modulation range of the simple telemetry system used. Resistor R2 limits the minimum output voltage from the chain.

The convenience of this arrangement is valuable in GSR measurement and monitoring in contexts other than carrying out the method of operating a computer system noted above. The input circuit for providing a linear output corresponding substantially to the logarithm of GSR constitutes a further feature of the invention.

The output voltage V2 from the buffer amplifier feeds the input of the following voltage controlled oscillator 5 section which generates a square wave output of frequency proportional to V2. The oscillator 5 output frequency can vary from about 100 to 400 Hz corresponding to input extremes of zero and infinite resistance at the electrodes but generally lies within the 150 to 350 Hz range in normal operation.

The square wave output from the oscillator 5 is fed to the pulse forming stage 6 which generates a rectangular pulse of about 15 microseconds duration following every negative going transition of the oscillator 5 output waveform. This output pulse turns on a transistor driver stage 7 which delivers a 15 microsecond 0,6 A current pulse to infrared emitting diodes 8. The transmitter is powered by a PP3 9V dry battery of about 400 mAH capacity allowing for at least 60 hours of operation before battery replacement.

Figure 4:
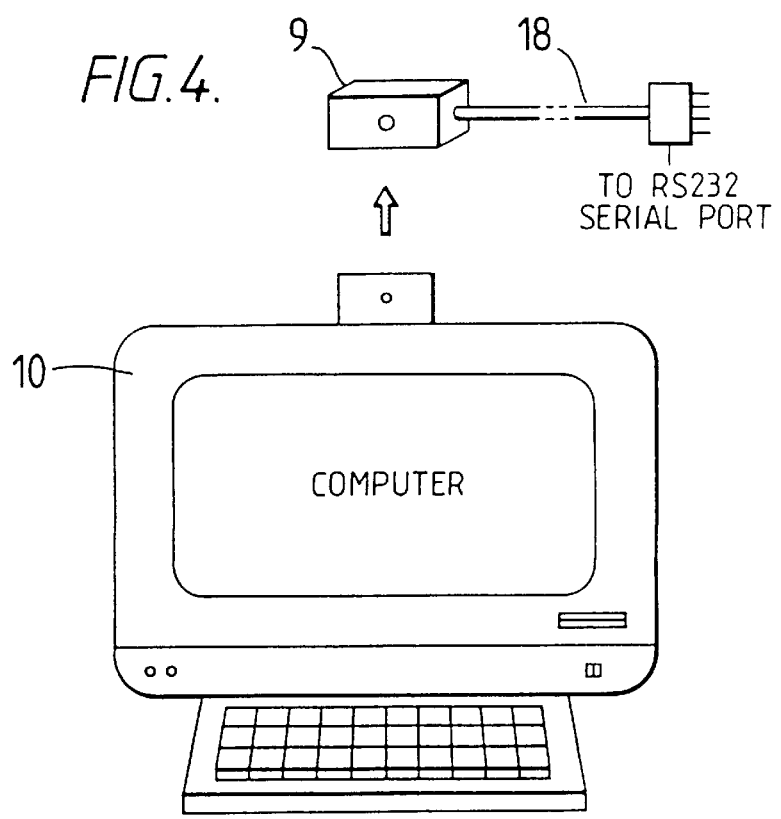
FIG. 4 is a diagram of portions of the apparatus of FIG. 1.
Figure 5:
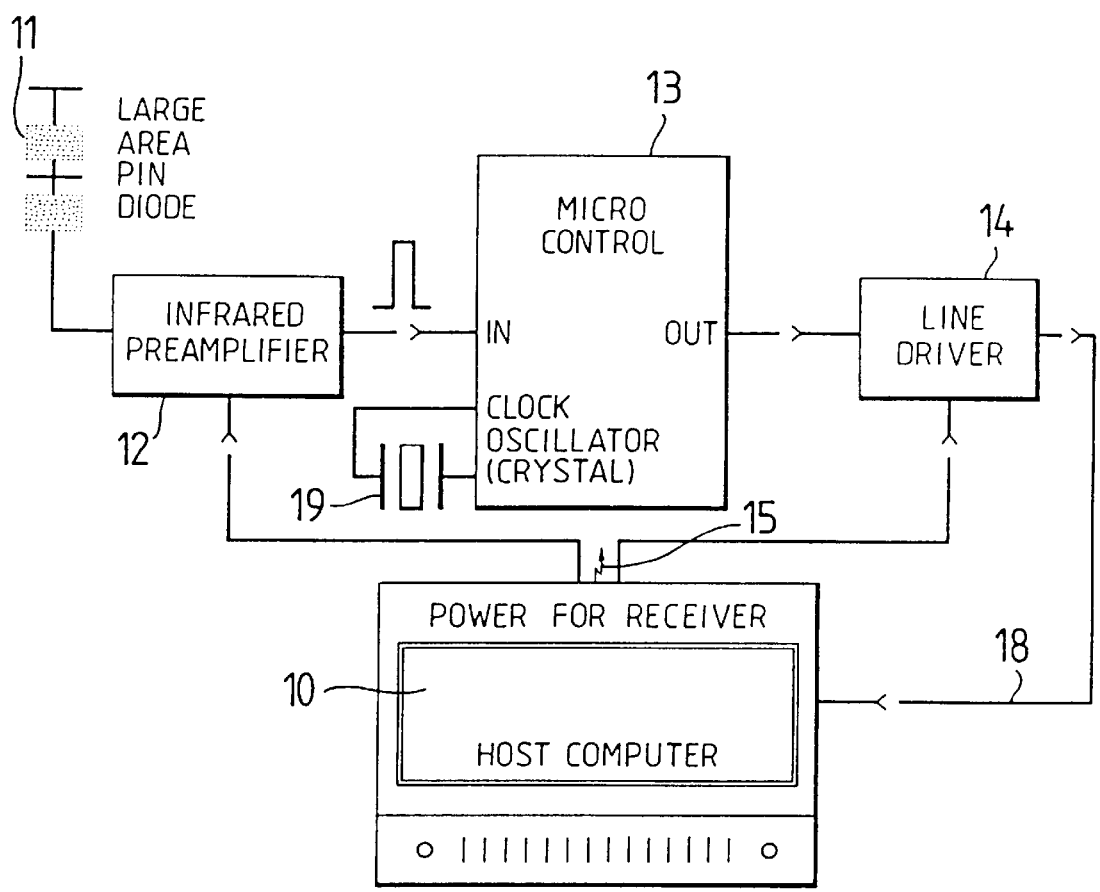
FIG. 5 is a diagram of an infrared telemetry receiver.

The receiver 9 is mounted in a small plastics box to be placed on top of a computer screen 10 (FIG. 4). Pulses of infrared radiation emitted by the transmitter 1 are detected by a reverse biased large area PIN photoelectrode 11 (FIG. 5) with integral infrared filter.

Photocurrent from the detector diode is fed to the input of an infrared pre-amplifier integrated circuit 12. The passband of this pre-amplifier is designed to reject the effects of unwanted infrared radiation, e.g. from sunlight, lighting fixtures and other interfering sources. A rectangular pulse of about 25 microseconds duration is generated at the pre-amplifier output following the reception of each pulse from the transmitter.

The pre-amplifier output pulses are fed to the input of a one-chip micro-controller 13 which counts the incoming pulses over a sampling period of about 95 milliseconds and then computes the corresponding pulse frequency to 12-bit precision. This value is then incorporated into two data bytes which are serially output from the micro-controller at a data rate of 9600 bits per second. Additional bits identify the most significant byte and flag the received signal quality.

A transistor line driver 14 then delivers this signal at the appropriate voltage levels through a receiver output cable 18 to a serial port RS232 of the host computer 10. Output sample rate is 10 per second. Output values sent from the receiver retain the quasi-logarithmic relation to the subject skin resistance. This can be expanded by the host computer if desired.

The micro-controller 13 operating programme incorporates several measures to maintain very low noise levels and good output recovery characteristics in spite of the effects of interference and subject movement.

These include the rejection of pulses arriving at irregular intervals and the handling of periods of signal loss which occurs particularly when the pre-amplifier automatic gain control sub-system cannot adapt fast enough to sudden reductions in received pulse intensity following subject movement. Poor reception quality as determined by received pulse regularity and other criteria applied within the micro-controller programme is signalled by an auxiliary bit within the information sent to the host computer 10 as determined by a clock oscillator 19.

The modest power requirements of the receiver are obtained from the host computer's communication port 15, eliminating the need for a separate receiver power supply.

The data is received as a standard RS232 input and for data processing 20 (FIG. 1) is specially encoded. Meanwhile, possible errors are detected and corrected. Then data is decoded and separated into status and parametric data. The parametric data is fed as an input to the analysing systems, which coordinate with animation, audio and other specialised systems determined by the programme being run in the computer.

The analysing system stores the data, which can be used to create various types, graphs and charts. These can be used to profile, compare or monitor the subject's accomplishment on-line or during subsequent analysis sessions.

Software for the computer can provide for a variety of psychological testing systems. For example, in an animation system 21 (FIG. 1), data is used to manipulate various segments of the computer screen. Changes in input data produce changes in the speed and path of animation. The procession of images encourages the user to continue adding to the metamorphic sequence in a logical and aesthetic way.

The animation system allows for different layers of skill (beginner, novice and expert). This ensures the adaptation of the system to the particular variations of the user. Therefore achievement, i.e. evolution of images, will take place even before expertise is acquired. In an audio system 21 (FIG. 1), there can be an option to have an audio response which includes both music and voice. This will also be integrated with the psycho-physiological input.

For a tutorial system 22 (FIG. 1), tutorial software is provided for a high quality interactive course (courseware). It consists of: i) a graded series of interactive lessons on the subject to be learnt; and ii) a comprehensive database facility which the program searches for giving answers, proposing new questions or entering a specific sub-routine. The lessons may then be presented through window prompts and animated sequences. In advanced models with video interface cards or videodisc players, video sequences can overlay graphics and animation.

The information handled in the tutorial via the database system 23 can be prepared with the help of leading professionals in the appropriate fields. The system therefore provides not only a training facility, but also a counselling mode based on expert knowledge.

Figure 6:
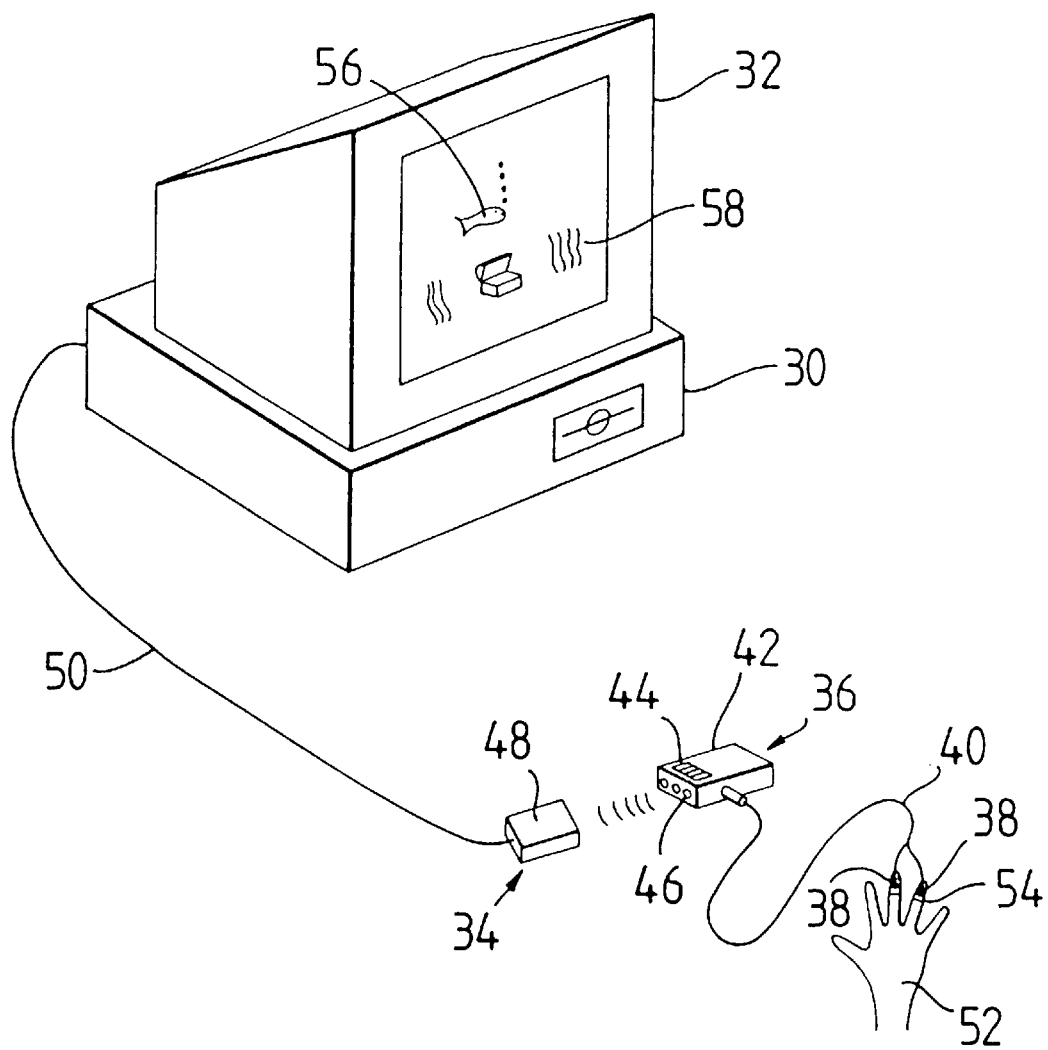
FIG. 6 is a schematic view of a particularly preferred embodiment of the present invention.
Figure 7:
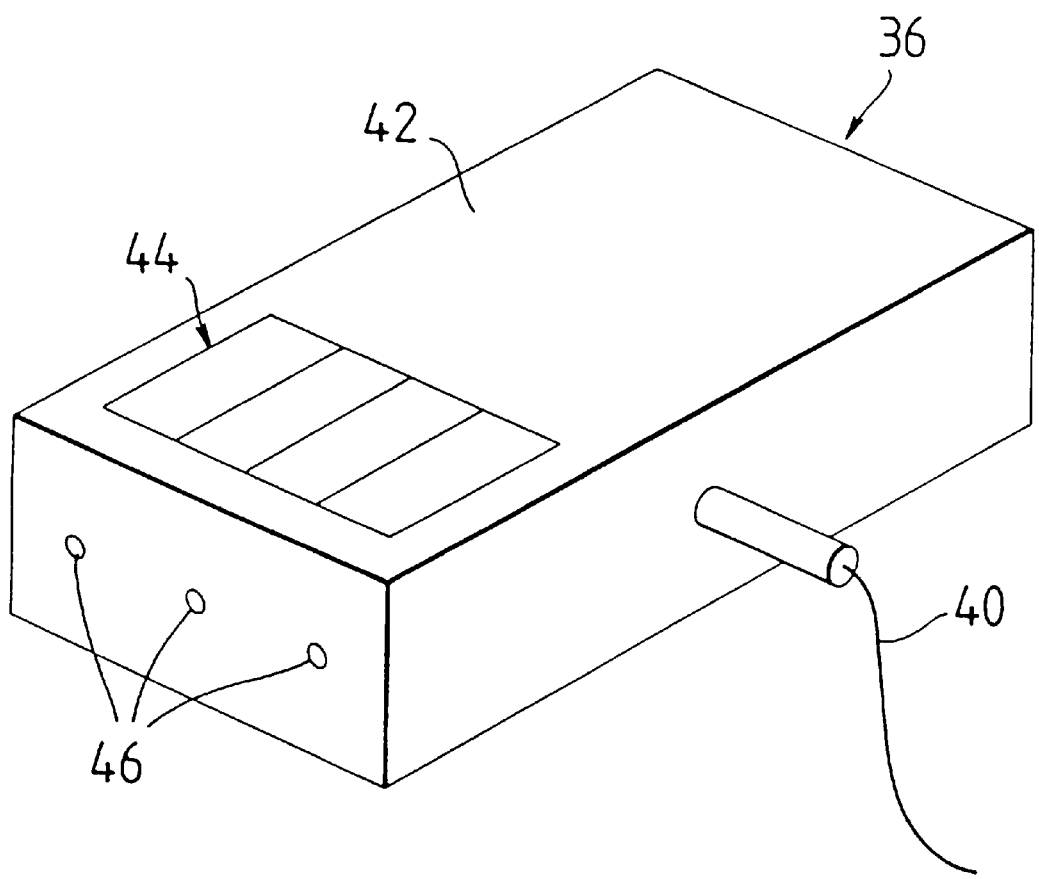
FIG. 7 is an enlarged view of a portion of FIG. 6.

FIGS. 6 and 7 show a particularly preferred embodiment of the present invention, comprising a computer 30, a monitor 32, a receiver 34 and a sensor unit 36.

Sensor unit 36 comprises a pair of non-invasive skin contact electrodes 38, connected by wires and a jack plug 40 to a sensor box 42. Sensor box 42 contains appropriate electronics (not shown) to convert the resistance between the electrodes 38 into a digital format signal. Sensor box 42 also contains switches 44 and infrared transmitters 46.

Receiving unit 34 comprises receiver box 48 and a wire and connector 50. The connector 50 connecting into a data entry port (not shown) on computer 30. This may be a standard serial communications part. Receiver box 48 contains an infrared receiver (not shown) and electronics appropriate to convert received infrared signals into computer usable form.

In use, electrodes 38 are applied to adjacent finger of a user's hand 52 and held in position by way of a band surrounding both electrode and finger 54. Band 54 is preferably of burr fastener material, but may be of any other suitable material. The electronics in sensor box 42, powered by a power source also contained in sensor box 42 (not shown) periodically assess the skin resistance of the user's hand 52 via electrodes 38. The electronics in sensor box 42 convert the readings of galvanic skin resistance into a data form suitable for transmission, and send the suitable data form to the infrared transmitters for transmission.

The infrared receiver in receiver box 48 receives the transmissions from infrared transmitters 46 and directs them to the electronics in receiver box 48. There the data is converted into a form suitable for inputting into the computer 30 which is running under the control of an appropriate computer program. In this particular preferred embodiment, the software running on computer 30 is generating on monitor 32 an image of a fish 56 swimming over a seascape 58. As the user becomes more relaxed, the user's galvanic skin resistance will rise. This will be detected by electrodes 38 and conveyed to the computer via sensor unit 36 and receiver unit 34. The software will generate graphics showing the fish swimming from left to right on the screen. As the fish 56 swims further to the right relative to the seascape 58, which scrolls to the left, the software is arranged to change the display so that the fish metamorphoses first into a mermaid then further into a human then an angel then a star. If, during this process, the user becomes less relaxed, so causing his galvanic skin resistance to drop, the fish, or whatever form it is at that time, travels to the left and the seascape scrolls to the right. The relative movement of fish 56 and seascape 58 enable the user to ascertain whether he or she is becoming more or less relaxed.

The software running on computer 30 may do more than simply show pictures of fishes 56 on seascapes 58. Switches 44 on sensor box 42 may be used to exert overall control over the software. For example, buttons 44 might represent an escape button to move the user out of a particular aspect of a program and into a menu, a pair of direction buttons to move around that menu once entered and an enter button to make selections from the menu. Such buttons enable the use of the customary keyboard forming part of the computer system to be dispensed with.

It will be obvious that the software running on computer 30 may have to set many different aspects relating to training, testing and assessment of the user.

Psycho-behavioural and Psychometric Test software may be used to programme the computer to provide a computerised testing facility which uses conventional methods of administration and interpretation. In addition, the system facilitates the on-line monitoring of psycho-physiological parameters. This last feature provides a method of detecting psycho-behavioural blockage-points during test completion. The interactive feedback of this information greatly enhances the training schedule.

It will be seen that the invention provides for all aspects of learning simultaneously in that it can involve the detection and analysis of both logic and intuitional processes; the first by monitoring "voluntary" action and the second by detecting "automatic" output. It uses psycho-physiological measurement principles to operate and interact with software applications by the use of an ergonomically designed sensor while the subject has freedom of movement and safety due to absence of actual contact between the subject and the computer.

We claim:

1. Apparatus for monitoring at least one psychophysiological parameter of at least one user's psychophysiological condition which provides an output display of a selected part of a continuous sequence of animated images viewable by said at least one user, the apparatus comprising a computer system; a program in the computer system adapted to store said sequence and to display a selected part of said sequence on a screen viewed by the at least one user; an input device comprising a sensor unit and receiver unit, wherein the sensor unit is adapted to monitor galvanic skin resistance of the at least one user and to transmit a value for said galvanic skin resistance monitored to the receiver unit, and wherein the receiver unit is adapted to input said value into the computer system; and software capable of using said value for said galvanic skin resistance as a control parameter to vary, in real time, the selected part of the sequence being displayed on said screen through continuing sequence in correspondence to the value thereby reflecting said at least one user's psychophysiological condition.

2. Apparatus according to claim 1 wherein the sensor unit is adapted to transmit data to the receiver unit via electromagnetic radiation.

3. Apparatus according to claim 2 wherein the electromagnetic radiation is in an infrared part of an electromagnetic spectrum.

4. Apparatus according to claim 3 wherein the receiver unit comprises a receiving diode, an infrared pre-amplifier and a micro-controller for converting received signals to a form acceptable to the computer system.

5. Apparatus as claimed in claim 1 wherein the sensor unit comprises non-invasive electrodes for applying to skin, circuitry appropriate to convert sensed skin resistance into digital data and means for transmitting the digital data to the receiving unit.

6. Apparatus according to claim 5 wherein the sensor unit is mounted on a wrist belt furnished with electrodes positioned to lie in contact with a wrist of the at least one user.

7. Apparatus according to claim 6 wherein the sensor unit is mounted in a case of a size to lie substantially within an area on the back of the wrist and contains a battery and microelectronic circuitry for forming pulses to be delivered to an infrared emitter diode.

\* \* \* \* \*